July 29, 1947. H. J. SYMONDS Plant Pat. 750
CARNATION PLANT
Filed May 10, 1946
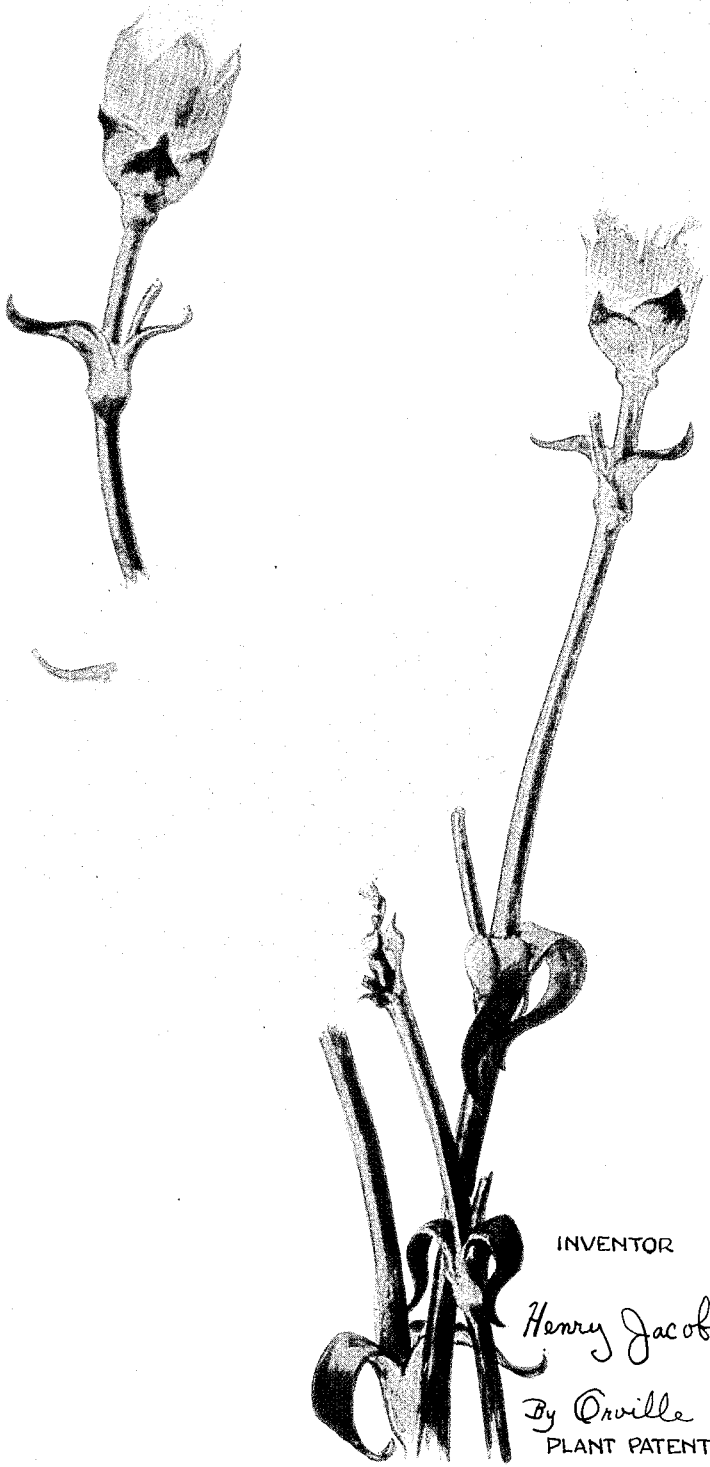
INVENTOR
Henry Jacob Symonds
By Orville M. Kile
PLANT PATENT AGENT Patented July 29, 1947

Plant Pat. 750

UNITED STATES PATENT OFFICE

750

CARNATION PLANT

Henry Jacob Symonds, Decorah, Iowa

Application May 10, 1946, Serial No. 668,649

1 Claim. (Cl. 47—60)

My present invention relates to improvements in carnation varieties ordinarily known as perpetual blooming or greenhouse forcing carnations. The object of my invention was the production of a variety having good growing and producing habits and a flower of novel color, medium size and pleasing fragrance. These features combine with other good features in my new variety.

My new variety was originated by hand-crossing two unnamed seedlings grown in my own greenhouses. It has been asexually reproduced for several seasons and its characteristics have persisted without change.

The accompanying illustrations show in full color three specimens of the flower of my new variety in different stages of opening, together with portions of the foliage and stems.

Following is a detailed description of the plant and flower of this new carnation variety. Color plate references are to Ridgway's Color Standards and Nomenclature.

*The plant*

Growth habits: Strong and vigorous, with no surplus growth. Usually attains a height of 36 to 40 inches.

Blooming habits: Exceptionally productive, since every shoot produces a bloom and the percentage of good blooms is very high. Comes into bloom medium early and blooms freely and continuously throughout the season.

Foliage:

*Size.*—Medium in width and length. Lower leaves approximately ½ inch wide.

*Color.*—Nickel Green (Plate XXXIII), with gray bloom.

*Coils.*—Leaves are relatively straight although some are curled.

Stems: Strong, straight, and medium heavy.

*Nodes.*—Medium sized.

*Color.*—Nickel Green.

*The flower*

Bud: Fat and rather short. Only moderately pointed.

Bloom:

*Size.*—Under good greenhouse conditions, attains a size of 3 to 3½ inches in diameter.

*Color.*—The general color effect might be called orchid-pink in the usual use of these color terms. When newly opened, the color in Ridgway's which approaches most nearly is Rosolane Pink (Plate XXVI), but as the flower ages it darkens slightly and becomes, on the second or third day, nearer to Pale Rosolane Purple (Plate XXVI).

*Form.*—Informal, with inner petals folded to give something of a sweet-pea likeness.

*Fragrance.*—Very intense clove fragrance.

*Petalage.*—In April there are from 28 to 35 petals.

*Petals.*—Regularly serrated; rounded on top. Shank comprises slightly less than half the entire petal length.

*Calyx.*—Consists of a single tube, 1¼ inches long, divided into five lobes. Has great strength and does not split. Color is Deep Yellow Green (Plate XXXII).

Reproductive organs:

*Ovary.*—Small, measuring about ¼ inch long. Set in a pithy cup ⅛ inch high, making the total height about ⅜ inch. The hard case of the ovary incloses many ovules.

*Pistils.*—Two pistils emerge from the top of the ovary. Styles are 1¼ inches long, white and curled at the tip.

*Stamens.*—Arising from the edge of the pithy cup are a few ragged stamens, a few of which are topped with yellowish anthers.

*Comparison*

The variety most like my new variety is the subject of Plant Patent No. 275. The principal differences between the two varieties are as follows:

1. The two varieties have entirely different parentage.

2. The foliage of my variety is not quite so wide, and its color is lighter than that of No. 275.

3. The nodes are not noticeably large in the stems of my new variety, while they are unusually large in the stems of No. 275.

4. The blooming season of my variety is not quite so early as that of No. 275.

5. The bud of my new variety is wider and more bulged.

6. The flower of my variety has fewer petals. There are 28 to 35 as compared with 45 to 50 in No. 275.

7. The form of the flower of my new variety is more irregular or informal.

8. The fragrance of the flower of my new variety is much more intense and has more of the clove characteristic.

9. The petals of the flower of my variety are more regularly serrated and are rounded at top rather than flattened.

Having thus disclosed my invention, I claim:

The new and distinct variety of carnation plant substantially as herein shown and described, characterized particularly by its exceedingly prolific growth and production habits, and the combination of medium size, intense fragrance and novel light orchid-pink color of its flowers.

HENRY JACOB SYMONDS.